United States Patent [19]
Umeda

[11] 3,943,922
[45] Mar. 16, 1976

[54] DRYING APPLIANCE FOR PREVENTING ATHLETE'S FOOT

[76] Inventor: Daihachiro Umeda, c/o Suzuki, No. 2-22-5, Fukagawa, Koto, Tokyo, Japan

[22] Filed: Dec. 30, 1974

[21] Appl. No.: 537,144

[30] Foreign Application Priority Data
Sept. 20, 1974   Japan.............................. 49-112633

[52] U.S. Cl................................ 128/81 R; 128/260
[51] Int. Cl.² ........................................... A61F 5/00
[58] Field of Search........... 128/260, 265, 81 R, 153

[56] References Cited
UNITED STATES PATENTS

| | | | |
|---|---|---|---|
| 2,595,640 | 5/1952 | Christopoulos................... | 128/81 R |
| 3,429,309 | 2/1969 | Kurth et al........................ | 128/81 R |

*Primary Examiner*—Lawrence W. Trapp

[57] ABSTRACT

A drying appliance for preventing athlete's foot, which is attached to the underside of the human toes and can absorb the moist, greasy and other secretions existing on the toes, on which a medicament can be applied and/or permeated.

4 Claims, 2 Drawing Figures

DRYING APPLIANCE FOR PREVENTING ATHLETE'S FOOT

BACKGROUND OF THE DISCLOSURE

The present invention relates to a drying appliance for preventing athlete's foot, which is attached to the underside of toes in order to absorb any moist or greasy secretion on the toes. Among the salesmen, car drivers and others who wear shoes for a long time all day, especially those who tend to perspire are being annoyed with their feet getting moist due to sweat or other secretions as well as with the subsequently bad smelling. Under such an unsanitary state they are getting easily athlete's feet between their toes. Once they have athlete's feet, it is very difficult to cure athlete's feet easy and soon. Nevertheless, till now any effective measure to cure athlete's foot has not been adopted. For instance, those who are annoyed with athlete's foot have applied a medicament between toes, and have used to put on the well-ventilated shoes or sandals. However, when they walk applying a cotton-made tape band to the athlete's foot, due to the move of toes it loses easily its own function of absorbing moistness, and finally is detached from the toes. Therefore, for the time being it is not easy to cure athlete's foot occurring at the underside of toes.

SUMMARY OF THE INVENTION

The present invention is carried out for the sake of overcoming the disadvantage described above.

The main object of the present invention is to provide a drying appliance which is firmly fixed to the underside of toes, and cannot be detached from it even if the toes are moved.

Another object of the present invention is to provide the drying appliance for preventing athlete's foot, which is made of such a specific shape and structure as to be fitted with various sizes of toes so that it cannot be detached from the underside of toes.

These and other features and advantages of the invention will be understood clearly from the following description in conjunction with the accompanying drawing.

DETAILED DESCRIPTION OF THE EMBODIMENT

Figure 1:
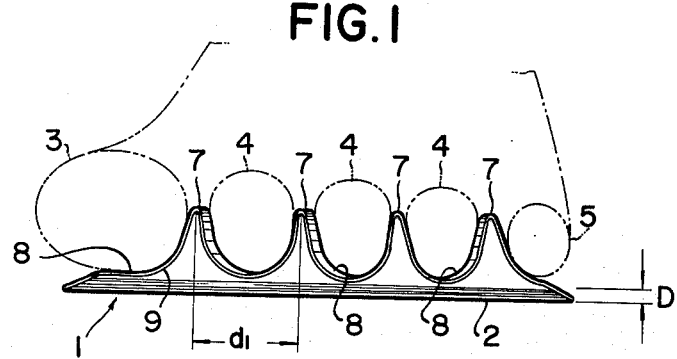
FIG. 1 is a front view showing how the drying appliance for preventing athlete's foot is fitted with the underside of toes.
Figure 2:
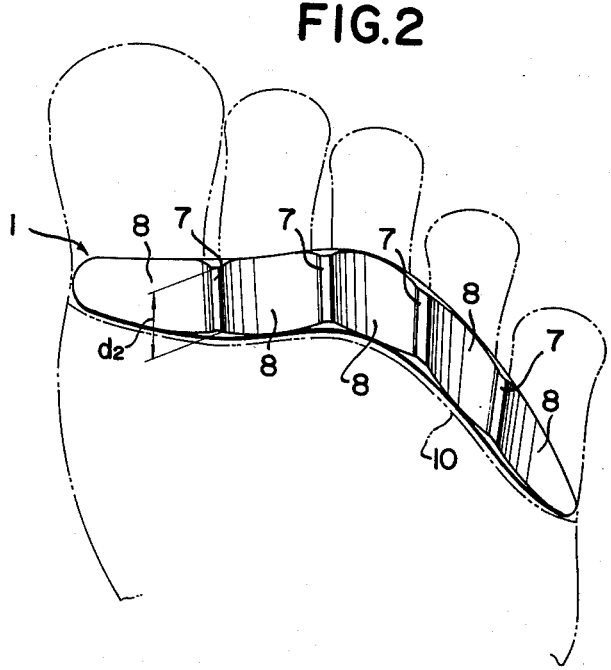
FIG. 2 is a plan view of the drying appliance for preventing athlete's foot.

An exemplary embodiment of the drying appliance for preventing athlete's foot according to the present invention will now be described in detail with reference to the illustrated drawing. In FIG. 1 the drying appliance for preventing athlete's foot has four convex portions 7 and five concave portions 8 on the base 2. The former 7 is inserted into each space 6 between toes (i.e. a big toe 3, three middle toes 4 and a little toe 5), and is held between toes. The latter 8 is attached to each underside of the five toes. And the drying appliance 1 is curved along a root line 10 of toes so as to correspond to the shape of the root of the five toes 3, 4, 5 as shown in FIG. 2.

The drying appliance for preventing athlete's foot may be made of a hygroscopic material such as fiber-shape paper and cotton, non-woven fabric consisting of a synthetic fiber of polyvinyl alcohol system and the like, on which a medicament can be applied and/or permeated. Alternatively, the base 2 can be separated from the convex and concave portions 7,8 combined with each other. In that case, the base 2 may be preferably made of somewhat rigid material as aforementioned so as to obtain its durability, while the convex and concave portions 7,8 may be made of a more soft material than that of the base 2, since they are directly fitted with the underside of the five toes. Then, the base 2 can be jointed with the convex and concave portions 7,8, on which surface a medicament can be applied and/or permeated. Alternatively, if an integral material consisting of the base 2 and the convex and concave portions 7,8 will be molded, it is possible to provide each appliance 1 by cutting the integral material so as to correspond to the curved line 10 of the root of toes. Alternatively, it is also possible to attach to the surface of the convex and concave portions 7,8 a band (i.e. a gauze) to which a medicament is applied.

In accordance with the size and shape of toes, the convex portions 7,8 can be adjusted. It is quite possible to manufacture the larger, middle and smaller sized appliance 1 consisting of the base and the convex and concave portions by changing the height of the convex portion 7 or the distance $d_1$ or the width $d_2$ or the thickness D of the base 2.

The function of the present invention will be now described. Once there is shaped a hygroscopic material such as fiber-shape paper and cotton, and non-woven fabric consisting of a synthetic fiber of polyvinyl alcohol system, it has flexibility to some extent, so that the shape of the hygroscopic material is not disordered. By making use of its flexibility as well as the height from the concave portion 8 to the convex portion 7, when the drying appliance 1 is applied to the underside of toes so as to be held between toes, i.e. in the space 6 between the two toes the drying appliance can be well fitted with the underside of toes, consequently being able to be used free from care.

As described above, this drying appliance for preventing athlete's foot is made of a hygroscopic material on which a medicament can be applied and/or permeated. In addition, the drying appliance has an appropriate shape so as to be able to be fitted with the human toes and its root, that is the shape having the convex and concave portions so as to correspond to the underside of toes. Also, it is possible to manufacture different sized appliances 1 in accordance with the size and shape of each person's toes. Further, it is easy to attach the appliance to the underside of toes or to detach it from the underside of toes. Further, even if one uses the appliance 1 for many hours or moves his own toes continuously, it is not detached easily from the underside of toes.

In addition, since the appliance 1 can be manufactured by means of mass-production, its cost is inexpensive so that it is replaceable with a new one. Consequently, from the sanitary point of view, the appliance 1 is advantageous. In this way, the drying appliance for preventing athlete's foot has many advantages in the practical use.

What I claimed is:

1. A disposable drying appliance for the toes of a foot for use to prevent athlete's foot, comprising a base member of stiff material which is permanently curved and bent to a general arc shape corresponding to the root of the toes and is adapted to be applied to the underside of the toes, said base member having upstanding flexible convex portions adapted to fit between the toes and defining adjacent concave portions adapted to receive the toes whereby the appliance is well-fitted to the underside of the toes, said base member and convex portions being constituted of a hygroscopic material capable of absorbing moisture.

2. A drying appliance as claimed in claim 1 wherein a medicament to prevent athlete's foot is introduced into the hygroscopic material.

3. A drying appliance as claimed in claim 2 and comprising four convex portions defining five concave portions, with the outer convex portions spaced inward from the outer concave portions.

4. A drying appliance as claimed in claim 1 wherein the appliance material is paper or cotton.

* * * * *